United States Patent
You et al.

(10) Patent No.: US 12,091,697 B2
(45) Date of Patent: Sep. 17, 2024

(54) ENZYMATIC PREPARATION OF GLUCOSAMINE

(71) Applicant: TIANJIN INSTITUTE OF INDUSTRIAL BIOTECHNOLOGY, CHINESE ACADEMY OF SCIENCES, Tianjin (CN)

(72) Inventors: Chun You, Tianjin (CN); Dongdong Meng, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 695 days.

(21) Appl. No.: 17/260,168

(22) PCT Filed: Jul. 11, 2019

(86) PCT No.: PCT/CN2019/095638
§ 371 (c)(1),
(2) Date: Jan. 13, 2021

(87) PCT Pub. No.: WO2020/011237
PCT Pub. Date: Jan. 16, 2020

(65) Prior Publication Data
US 2021/0277437 A1   Sep. 9, 2021

(30) Foreign Application Priority Data
Jul. 13, 2018   (CN) .......................... 201810772487.3

(51) Int. Cl.
*C12P 19/26* (2006.01)
*C12P 19/28* (2006.01)

(52) U.S. Cl.
CPC ....... *C12P 19/26* (2013.01); *C12Y 204/01001* (2013.01); *C12Y 204/01007* (2013.01); *C12Y 204/0102* (2013.01); *C12Y 204/01049* (2013.01); *C12Y 305/99006* (2013.01); *C12Y 503/01009* (2013.01); *C12Y 504/02002* (2013.01)

(58) Field of Classification Search
None
See application file for complete search history.

(56) References Cited

U.S. PATENT DOCUMENTS

2005/0042734 A1* 2/2005 Bao .......................... C12P 19/26
435/85

FOREIGN PATENT DOCUMENTS

| CN | 1314951 A | 9/2001 |
|---|---|---|
| CN | 1685054 A | 10/2005 |
| CN | 106148425 A | 11/2016 |
| CN | 107815444 A | 3/2018 |
| EP | 1923464 A1 | 5/2008 |
| JP | 2005198625 A | 7/2005 |
| JP | 5424604 B2 | 2/2014 |

OTHER PUBLICATIONS

Harada ("Isoamylase and its industrial Significance in the Production of Sugars from Starch", Biotechnology and Genetic Engineering Reviews, 1984, 1:1, 39-64), (Year: 1984).*
Sigma ("Enzymatic Assay of Phosphorylase a (EC 2.4.1.1)", Sigma Aldrich, 1994, available at https://www.sigmaaldrich.com/US/en/product/sigma/p1261 ). (Year: 1994).*
Zhang (CN106148425A, English language translation provided courtesy of Espacenet, 2016) (Year: 2016).*
Uniprot, ("P0A759" available at https://www.uniprot.org/uniprotkb/P0A759/entry, accessed on Sep. 23, 2023). (Year: 2023).*
Liu, Dianlei et al.; Research Advance of the Construction of Gene Engineering Strains for Glucosamine; Biotechnology Bulletin, No. 3, Dec. 31, 2014, pp. 36-41.
Fukui, T. et al. Predicted sugar phosphatase, HAD superfamily [Thermococcus kodakarensis KOD1]; GenBank: BAD85923.1,Oct. 7, 2016, Features, Origin.
Liu, L. et al. Microbial production of glucosamine and N-acetylglucosamine: advances and perspectives Appl. Microbiol. Biotechnol., vol. 97, Jun. 11, 2013, pp. 6149-6158.
You, C, et al.; Simple cloning via direct transformation of PCR product (DNA Multimer) to *Escherichia coli* and Bacillus subtilis. Applied and Environmental Microbiology 78(5):1593-5.
Cheng, K. et al.; Doubling Power Output of Starch Biobattery Treated by the Most Thermostable Isoamylase from an Archaeon Sulfolobus tokodaii; Scientific Reports. 5:13184, Aug. 20, 2015.

* cited by examiner

*Primary Examiner* — Robert J Yamasaki
*Assistant Examiner* — Charles Zoltan Constantine
(74) *Attorney, Agent, or Firm* — NKL Law; Allen Xue

(57) ABSTRACT

A method for preparing glucosamine includes the steps of converting fructose-6-phosphate (F6P) and an ammonium salt to glucosamine-6-phosphate (GlcN6P) under the catalysis of glucosamine-6-phosphate deaminase (EC 3.5.99.6, GlmD); and producing glucosamine (GlcN) by the dephosphorylation of GlcN6P under the catalysis of an enzyme capable of catalyzing the dephosphorylation. Such a method can be used to prepare glucosamine by in vitro enzymatic biosystem.

22 Claims, 5 Drawing Sheets
Specification includes a Sequence Listing.

SEQUENCE LISTING

<160> NUMBER OF SEQ ID NOS: 2

<210> SEQ ID NO 1
<211> LENGTH: 807
<212> TYPE: DNA
<213> ORGANISM: Thermococcus kodakarensis

<400> SEQUENCE: 1

```
atgacgagaa aaatcggcat tatcttcgac atggacggcg tcatctacag aggcagcgag      60
ccgataaatg gtgcaaaaga ggtcatcgag ttcctgaaag aaaggaaaat acccttcctg     120
```

```
ttcctcacga acaactccac gagagacccc gcaatgtaca gggaaaagct cctctcgatg    180
ggcatagacg tgccggaaga tgttatagtc acgtcgggcc tggccacgag gctctacatg    240
gagaagcact ttgagccagg agaagttttc gttatcggtg aaagggggct ctcagggag     300 atggagcgcc tcggctgggg agttgttagc cttgaagatg ctaggaaagg cgcctggaag    360
aggatcaagc acgtcgttgt gggccttgac cccgagttaa cctacgagaa gctcaagtac    420
ggaacgctcg ctataaggaa cggggcaagc ttcatagggga cgaaccccgga cacgacatat   480 ccagcggagg aagggctcta ccccggtgct ggggcaataa tagccgccct cagggcatca    540
acggacagag agccagtgat cataggcaag ccaaacgaac cggcctatga agtcgttaag    600
gacaaacttg gagacgttga agagctctgg atggtcggcg acaggctcga taccgatata    660
gcgttcgcaa agcgcttcgg catgaaggcc ataatggtgc tcacgggtgt aagcacgctc    720
aaggacgttg ccgaaagcgg gataaagccg aacctcgttc tccccgatgt gggggagctg    780
aaaaggtatc tggaggctgc cctttag                                       807

<210> SEQ ID NO 2
<211> LENGTH: 268
<212> TYPE: PRT
<213> ORGANISM: Thermococcus kodakarensis

<400> SEQUENCE: 2

Met Thr Arg Lys Ile Gly Ile Ile Phe Asp Met Asp Gly Val Ile Tyr
1               5                   10                  15

Arg Gly Ser Glu Pro Ile Asn Gly Ala Lys Glu Val Ile Glu Phe Leu
            20                  25                  30

Lys Glu Arg Lys Ile Pro Phe Leu Phe Leu Thr Asn Asn Ser Thr Arg
        35                  40                  45

Asp Pro Ala Met Tyr Arg Glu Lys Leu Leu Ser Met Gly Ile Asp Val
    50                  55                  60

Pro Glu Asp Val Ile Val Thr Ser Gly Leu Ala Thr Arg Leu Tyr Met
65                  70                  75                  80

Glu Lys His Phe Glu Pro Gly Glu Val Phe Val Ile Gly Gly Lys Gly
                85                  90                  95

Leu Leu Arg Glu Met Glu Arg Leu Gly Trp Gly Val Val Ser Leu Glu
            100                 105                 110

Asp Ala Arg Lys Gly Ala Trp Lys Arg Ile Lys His Val Val Val Gly
        115                 120                 125

Leu Asp Pro Glu Leu Thr Tyr Glu Lys Leu Lys Tyr Gly Thr Leu Ala
    130                 135                 140

Ile Arg Asn Gly Ala Ser Phe Ile Gly Thr Asn Pro Asp Thr Thr Tyr
145                 150                 155                 160

Pro Ala Glu Glu Gly Leu Tyr Pro Gly Ala Gly Ala Ile Ile Ala Ala
                165                 170                 175

Leu Arg Ala Ser Thr Asp Arg Glu Pro Val Ile Ile Gly Lys Pro Asn
            180                 185                 190

Glu Pro Ala Tyr Glu Val Val Lys Asp Lys Leu Gly Asp Val Glu Glu
        195                 200                 205

Leu Trp Met Val Gly Asp Arg Leu Asp Thr Asp Ile Ala Phe Ala Lys
    210                 215                 220

Arg Phe Gly Met Lys Ala Ile Met Val Leu Thr Gly Val Ser Thr Leu
225                 230                 235                 240
```

```
Lys Asp Val Ala Glu Ser Gly Ile Lys Pro Asn Leu Val Leu Pro Asp
                245                 250                 255
Val Gly Glu Leu Lys Arg Tyr Leu Glu Ala Ala Leu
            260                 265
```

ENZYMATIC PREPARATION OF GLUCOSAMINE

CROSS-REFERENCE TO RELATED APPLICATIONS

This application is a U.S. national phase of International Application No. PCT/CN2019/095638, filed Jul. 11, 2019, which claims the priority of the prior application with a patent application number of CN 201810772487.3 and an invention title of "enzymatic preparation of glucosamine" as filed with the China National Intellectual Property Administration on Jul. 13, 2018. The prior application is incorporated in its entirety herein by reference.

INCORPORATION OF SEQUENCE LISTING

This application contains a sequence listing submitted in Computer Readable Form (CRF). The CRF file containing the sequence listing entitled "PA150-0094_ST25.txt", which was created on Jan. 12, 2021, and is 3,886 bytes in size. The information in the sequence listing is incorporated herein by reference in its entirety.

FIELD OF THE INVENTION

The present invention relates to a method for preparing glucosamine, especially to a method for preparing glucosamine by in vitro enzymatic biosystem, which belongs to the field of enzymatic preparation of glucosamine.

BACKGROUND OF THE INVENTION

Glucosamine is a compound obtained by substituting the hydroxyl at the 2-position of a D-glucose molecule with amino, and is an important functional monosaccharide. Glucosamine is present in almost all organisms, including bacteria, yeasts, filamentous fungi, plants and animals, and is a major component of glycoproteins and proteoglycans, as well as a major component of chitosan and chitin.

Glucosamine and derivatives thereof have wide application, and have important application in medicine, food, cosmetics and other fields. In pharmaceutical industry, glucosamine sulphate can stimulate the biosynthesis of cartilage proteoglycans and thus can be used as a drug substance for the treatment of rheumatoid arthritis; in food industry, glucosamine has various physiological functions including absorbing free radicals generated in vivo, resisting aging, promoting weight loss, inhibiting bacteria, regulating endocrine of human body and the like, and is used in the production of food additives and health food; and in cosmetic industry, acetylglucosamine (GlcNAc) as a monomer of hyaluronic acid is an indispensable substance in high-grade cosmetics at present.

Currently, there are two main methods for preparing glucosamine. (1) Chitin hydrolysis method, including chitin acid hydrolysis method and chitin enzyme hydrolysis method. The chitin acid hydrolysis method is the most commonly used method for preparing glucosamine, which comprises hydrolyzing chitin with high-concentration hydrochloric acid to obtain acetylglucosamine, and then deacetylating the acetylglucosamine to obtain glucosamine. The preparation method is influenced by raw material supply, and causes serious environmental pollution owing to the wastewater generated by acid treatment. In addition, people who are allergic to prawn and crab raw material may have allergic reaction after consuming the glucosamine prepared by the method. The chitin enzyme hydrolysis method takes chitin as raw material, and generates glucosamine monomer through hydrolysis reaction under chitin enzyme. The method has less environmental pollution, but is also limited by various factors including raw material supply, low production intensity, causing allergic reaction and the like. (2) Microbial fermentation method, which mainly uses engineering bacteria such as *Escherichia coli, Bacillus subtilis* to metabolize glucose and other raw materials to prepare glucosamine. The method is not restricted by the source of raw materials, has short fermentation time and low environmental pollution, is safety to human body, and the like advantages; however, it has the defects of difficult metabolic modification of microbial engineering bacteria, easy generation of metabolic byproducts and the like.

Therefore, it is highly desirable to develop a new method for preparing glucosamine with low cost and low pollution.

SUMMARY OF THE INVENTION

The present invention relates to a method for preparing glucosamine by an in vitro enzymatic method, wherein the method uses an in vitro enzymatic biosystem to produce glucosamine. The method has the advantages of cheap raw materials, rich raw material sources, low production cost, environmental friendliness, safety to human body and the like.

The present invention is realized by the following technical solutions:

The present invention provides a method for preparing glucosamine by using an in vitro enzymatic reaction comprising: converting fructose-6-phosphate (F6P) and an ammonium salt to glucosamine-6-phosphate (GlcN6P) under the catalysis of a glucosamine-6-phosphate deaminase (EC 3.5.99.6, GlmD); and producing glucosamine (GlcN) by the dephosphorylation of GlcN6P under the catalysis of an enzyme capable of catalyzing the dephosphorylation.

According to the present invention, various ammonium salts can be used herein. Preferably, the ammonium salt may be one selected from the group consisting of ammonium sulfate, ammonium chloride, ammonium bisulfate, ammonium nitrate, ammonium carbonate, and ammonium bicarbonate, or any mixture of two or more selected from the group.

According to the present invention, preferably, the method further comprises a reaction step of converting glucose-6-phosphate (G6P) to F6P, which is catalyzed by phosphoglucose isomerase (EC 5.3.1.9, PGI).

According to the present invention, preferably, the method further comprises a reaction step of converting glucose-1-phosphate (G1P) to G6P, which is catalyzed by a phosphoglucomutase (EC 5.4.2.2, PGM).

According to the present invention, preferably, the method further comprises a reaction step of converting a substrate and a phosphate to G1P, wherein the substrate may be a disaccharide or polysaccharide containing D-glucose units, or any mixture of the disaccharide and polysaccharide. In this step, an enzyme capable of converting the substrate and phosphate to G1P is used for catalysis.

According to the present invention, various phosphates can be used herein. Preferably, the phosphate may be one selected from the group consisting of potassium dihydrogen phosphate, dipotassium hydrogen phosphate, sodium dihydrogen phosphate, and disodium hydrogen phosphate, or any mixture of two or more selected from the group. More preferably, the phosphate is potassium dihydrogen phosphate and/or dipotassium hydrogen phosphate.

According to the present invention, preferably, the disaccharide containing D-glucose units is sucrose, and a sucrose phosphorylase (EC 2.4.1.7, SP) is used to catalyze the conversion of sucrose and a phosphate to G1P.

According to the present invention, preferably, the polysaccharide containing D-glucose units may be selected from starch, starch derivatives or any mixture thereof, and an α-glucan phosphorylase (EC 2.4.1.1, αGP) is used to catalyze the conversion of the polysaccharide containing D-glucose units and a phosphate to G1P. Preferably, the starch or starch derivative is selected from the group consisting of soluble starch, soluble amylose, soluble amylopectin, starch dextrin, maltodextrin, and maltopolysaccharide. Preferably, the starch is a soluble starch.

According to the present invention, preferably, the polysaccharide containing D-glucose units may also be selected from cellulose, cellulose derivatives or any mixture thereof. Preferably, the cellulose derivative may be selected from cellodextrin, cellobiose or any mixture thereof. Preferably, the cellulose derivative is a product of cellulose after acid or enzyme pretreatment, and the product is cellodextrin, cellobiose or any mixture thereof. Preferably, the cellulose derivative is cellodextrin. When the polysaccharide containing D-glucose units comprises cellulose and/or cellodextrin, for example, when it is cellulose and/or cellodextrin, a cellodextrin phosphorylase (EC 2.4.1.49, CDP) is used to catalyze the conversion of the polysaccharide containing D-glucose units and a phosphate to G1P; preferably, a cellobiose phosphorylase (EC 2.4.1.20, CBP) is further used to catalyze the conversion of cellobiose produced by the degradation of cellulose and/or cellodextrin and a phosphate to G1P. When the polysaccharide containing D-glucose units comprises cellobiose, for example, when it is cellobiose, a cellobiose phosphorylase (EC 2.4.1.20, CBP) is used to catalyze the conversion of the polysaccharide containing D-glucose units and a phosphate to G1P.

Those skilled in the art can understand that the above-mentioned steps comprised in the method of the present invention can be carried out step by step, for example, they can be carried out in one bioreactor or reaction vessel or in multiple bioreactors or reaction vessels arranged in series.

Those skilled in the art can understand that the above-mentioned steps comprised in the method of the present invention can also be carried out simultaneously, for example, they can be carried out in one bioreactor or reaction vessel. Preferably, the above-mentioned steps comprised in the method of the present invention are carried out simultaneously.

Preferably, the present invention provides a method for preparing glucosamine by using an in vitro enzymatic reaction comprising: taking disaccharide or polysaccharide containing D-glucose units or any mixture thereof as the substrate, adding a phosphate, an ammonium salt, an enzyme capable of converting the disaccharide or polysaccharide containing D-glucose units or any mixture thereof and the phosphate to G1P, a phosphoglucomutase, a phosphoglucose isomerase, glucosamine-6-phosphate deaminase and an enzyme capable of catalyzing the dephosphorylation, and going through catalytic reaction to obtain glucosamine.

Those skilled in the art can understand that glucosamine-6-phosphate deaminases from various sources can be used in the present invention. Preferably, the glucosamine-6-phosphate deaminase can be derived from *Escherichia coli* (UniProt No. P0A759), *Bacillus subtilis* (UniProt No. O35000), *Giardia lamblia* (UniProt No. V6TL01), *Thermococcus kodakarensis* (UniProt No. Q5JDU3) or the like.

Those skilled in the art can understand that enzymes capable of catalyzing the dephosphorylation from various sources can be used in the present invention. According to one aspect of the present invention, the enzyme capable of catalyzing the dephosphorylation is a glucosamine-6-phosphate phosphatase (GlmP) with substrate specificity. Preferably, the glucosamine-6-phosphate phosphatase can be derived from *Escherichia coli* (UniProt Nos. P77475, P27848, P0AE22, etc.), *Bacteroides thetaiotaomicron* (UniProt No. Q8A759) or the like.

The thermophilic enzyme UniProt No. Q5JJ45 derived from *Thermococcus kodakarensis* is annotated as sugar phosphatase (HAD superfamily), having a nucleotide sequence as shown in SEQ ID NO: 1, and an amino acid sequence as shown in SEQ ID NO: 2. In the present invention, the substrate specificity of Q5JJ45 has been identified, and the result shows that Q5JJ45 is a heat-resistant enzyme capable of catalyzing the dephosphorylation of GlcN6P and has the function of catalyzing GlcN6P to produce glucosamine. According to another aspect of the present invention, the enzyme capable of catalyzing the dephosphorylation is encoded by a nucleotide comprising a nucleotide sequence having at least 60%, at least 70%, at least 80%, at least 90%, at least 95%, at least 99% or 100% sequence identity with SEQ ID NO: 1; preferably, the nucleotide is a nucleotide sequence having at least 60%, at least 70%, at least 80%, at least 90%, at least 95%, at least 99% or 100% sequence identity with SEQ ID NO: 1. Preferably, the enzyme capable of catalyzing the dephosphorylation comprises an amino acid sequence having at least 60%, at least 70%, at least 80%, at least 90%, at least 95%, at least 99% or 100% sequence identity with SEQ ID NO: 2; preferably, the enzyme capable of catalyzing the dephosphorylation has an amino acid sequence having at least 60%, at least 70%, at least 80%, at least 90%, at least 95%, at least 99% or 100% sequence identity with SEQ ID NO: 2. Preferably, the enzyme capable of catalyzing the dephosphorylation is a sugar phosphatase derived from *Thermococcus kodakarensis* (UniProt No. Q5JJ45).

Those skilled in the art can understand that enzymes capable of converting a substrate to G1P, phosphoglucomutases, and phosphoglucose isomerases from various sources can be used in the present invention. Preferably, the α-glucan phosphorylase may be derived from *Escherichia coli* (Uniprot No. AOAOAOHB49), *Thermotoga maritima* (Uniprot No. G4FEH8), *Clostridium thermocellum* (Uniprot No. A3DCB6) or the like; the sucrose phosphorylase may be derived from *Bifidobacterium adolescentis* (Uniprot No. A0ZZH6), *Thermoanaerobacterium thermosaccharolyticum* (UniProt No. D9TT09) or the like; the cellodextrin phosphorylase may be derived from *Clostridium thermocellum* (UniProt No. A3DJQ6), *Clostridium stercorarium* (UniProt No. P77846) or the like; the cellobiose phosphorylase may be derived from *Clostridium thermocellum* (UniProt No. A3DC35), *Thermotoga neapolitana* (UniProt No. B9K7M6) or the like. The phosphoglucomutase may be derived from *Clostridium thermocellum* (Uniprot No. A3DEW8), *Thermococcus kodakarensis* (UniProt No. Q68BJ6) or the like; and the phosphoglucose isomerase may be derived from *Clostridium thermocellum* (Uniprot No. A3DBX9), *Thermus thermophilus* (Uniprot No. Q5SLL6) or the like.

According to the present invention, preferably, the catalytic reaction is carried out at a temperature of 30-70° C., more preferably 30-50° C., and most preferably 37° C.

According to the present invention, preferably, the pH of the catalytic reaction is 5.0-8.0, more preferably 6.0-7.5, and most preferably 7.0.

According to the present invention, when the above-mentioned steps are carried out simultaneously, preferably, the catalytic reaction time is 1-48 h, further preferably 8-36 h, more preferably 10-24 h, and most preferably 20 h.

According to the present invention, when the above-mentioned steps are carried out step by step, preferably, the catalytic reaction time in each step is independently 0.5-10 h, further preferably 1-3 h, and most preferably 2 h.

According to the present invention, preferably, the concentration of the substrate in the reaction system is 1-200 g/L, further preferably 5-50 g/L, more preferably 8-20 g/L, and most preferably 10 g/L.

According to the present invention, preferably, the concentration of the enzyme capable of converting a substrate to G1P in the reaction system is 0.1-10 U/mL, further preferably 0.2-5 U/mL, more preferably 1-3 U/mL, and most preferably 2 U/mL; preferably, the concentration of the phosphoglucomutase is 0.1-10 U/mL, further preferably 0.2-5 U/mL, more preferably 1-3 U/mL, and most preferably 2 U/mL; preferably, the concentration of the phosphoglucose isomerase is 0.1-10 U/mL, more preferably 1-5 U/mL, and most preferably 3 U/mL; preferably, the concentration of the glucosamine-6-phosphate deaminase is 0.1-10 U/mL, further preferably 0.2-5 U/mL, more preferably 1-3 U/mL, and most preferably 2 U/mL; preferably, the concentration of the enzyme capable of catalyzing the dephosphorylation is 0.1-10 U/mL, further preferably 0.2-5 U/mL, more preferably 1-3 U/mL, and most preferably 2 U/mL.

According to the present invention, preferably, the concentration of the ammonium salt in the reaction system is 50-500 mM, more preferably 100-300 mM, and most preferably 200 mM.

According to the present invention, preferably, the concentration of the phosphate in the reaction system is 1-150 mM, further preferably 2-50 mM, more preferably 10-30 mM, and most preferably 20 mM. Those skilled in the art can understand that the phosphate produced during the process of dephosphorylation of GlcN6P to produce glucosamine (GlcN) can be used as a phosphorus source in the step of converting a disaccharide or polysaccharide containing D-glucose units or any mixture thereof to G1P.

According to the present invention, preferably, the above reaction system further comprises a magnesium salt. Those skilled in the art can understand that various magnesium salts can be used in the present invention, such as magnesium chloride, magnesium sulfate and the like; preferably, the magnesium salt is magnesium chloride. Preferably, the concentration of the magnesium salt in the reaction system is 1-20 mM, further preferably 2-15 mM, and most preferably 10 mM.

According to the present invention, preferably, the above reaction system further comprises a buffer. Those skilled in the art can understand that various buffers can be used in the present invention, such as HEPES buffer, Tris-HCl buffer, MOPS buffer, citrate buffer such as sodium citrate buffer and the like. Preferably, the buffer is HEPES buffer. Preferably, the concentration of the buffer in the reaction system is 20-300 mM, preferably 50-200 mM, and most preferably 100 mM.

According to the present invention, the catalytic reaction is carried out without the presence of ATP and NAD(H).

In a preferred embodiment, when the starch, starch derivatives or any mixture thereof contains α-1,6-glycosidic bonds (for example, soluble starch, soluble amylopectin, starch dextrin, maltodextrin, or maltopolysaccharide), the method of the present invention also comprises a reaction step of hydrolyzing the α-1,6-glycosidic bonds in the substrate by using an isoamylase (EC 3.2.1.68, IA).

Those skilled in the art can understand that isoamylases from various sources can be used in the present invention. Preferably, the isoamylase may be derived from *Sulfolobus tokodaii* (UniProt No. Q973H3), *Flavobacterium* sp. (UniProt No. O32611) or the like.

According to the present invention, preferably, the concentration of the isoamylase in the reaction system is 0.1-10 U/mL, more preferably 0.5-2 U/mL, and most preferably 1 U/mL.

Those skilled in the art can understand that the reaction step of hydrolyzing the α-1,6-glycosidic bonds in the substrate by using an isoamylase and the above-mentioned reaction steps can be carried out step by step, for example, they can be carried out in one bioreactor or reaction vessel or in multiple bioreactors or reaction vessels arranged in series. Alternatively, the reaction step of hydrolyzing the α-1,6-glycosidic bonds in the substrate by using an isoamylase and the above-mentioned reaction steps can also be carried out simultaneously, for example, they can be carried out in one bioreactor or reaction vessel.

Preferably, the reaction step of hydrolyzing the α-1,6-glycosidic bonds in the substrate by using an isoamylase is carried out before the reaction step of converting the substrate and the phosphate to G1P; that is, firstly hydrolyzing the α-1,6-glycosidic bonds in the substrate by using an isoamylase, to obtain an isoamylase-treated substrate, and then carrying out other reaction steps, wherein, other reaction steps can be carried out step by step or simultaneously. At this time, preferably, the concentration of the substrate in the reaction system is 1-300 g/L, further preferably 10-200 g/L, more preferably 50-150 g/L, and most preferably 100 g/L; preferably, the concentration of the isoamylase is 0.1-10 U/mL, more preferably 0.5-2 U/mL, and most preferably 1 U/mL; preferably, the pH of the catalytic reaction is 4-8, more preferably 4.5-6.5, and most preferably 5.5; preferably, the reaction is carried out at a temperature of 10-99° C. for 0.5-72 h, further preferably at a temperature of 30-95° C. for 1-48 h, more preferably at a temperature of 50-90° C. for 6-24 h, and most preferably at 85° C. for 12 h. Preferably, the reaction system further comprises a magnesium salt and a buffer. Those skilled in the art can understand that various magnesium salts can be used in the present invention, such as magnesium chloride, magnesium sulfate or the like; preferably, the magnesium salt is magnesium chloride. Preferably, the concentration of the magnesium salt in the reaction system is 0.01-10 mM, further preferably 0.1-5 mM, more preferably 0.2-1 mM, and most preferably 0.5 mM. Those skilled in the art can understand that various buffers can be used in the present invention, such as sodium acetate buffer, HEPES buffer, citrate buffer such as sodium citrate buffer or the like; preferably, the buffer is sodium acetate buffer. Preferably, the concentration of the buffer in the reaction system is 1-50 mM, further preferably 2-20 mM, more preferably 3-10 mM, and most preferably 5 mM.

In a preferred embodiment, when the substrate is starch, starch derivatives or any mixture thereof (for example, soluble starch, soluble amylose, soluble amylopectin, starch dextrin, maltodextrin, or maltopolysaccharide), the method of the present invention also comprises a reaction step catalyzed by a 4-α-glucanotransferase (EC 2.4.1.25, 4GT).

Those skilled in the art can understand that 4-α-glucanotransferases from various sources can be used in the present invention. Preferably, the 4-α-glucanotransferase may be derived from *Thermococcus litoralis* (UniProt No. O32462), *Bacillus subtilis* (UniProt No. L8AG91), *Clostridium butyricum* (UniProt No. Q59266) or the like.

According to the present invention, preferably, the concentration of the 4-α-glucanotransferase in the reaction system is 0.1-10 U/mL, further preferably 0.2-5 U/mL, more preferably 0.5-2 U/mL, and most preferably 1 U/mL.

Those skilled in the art can understand that the reaction step catalyzed by a 4-α-glucanotransferase and the above-mentioned steps can be carried out step by step, for example, they can be carried out in one bioreactor or reaction vessel or in multiple bioreactors or reaction vessels arranged in series. Alternatively, the reaction step catalyzed by a 4-α-glucanotransferase and the above-mentioned reaction steps can also be carried out simultaneously, for example, they can be carried out in one bioreactor or reaction vessel.

Preferably, the reaction step catalyzed by a 4-α-glucanotransferase is carried out after the reaction of converting the substrate and phosphate to G1P has been carried out for a period of time. At this time, preferably, after the reaction of converting the substrate and phosphate to G1P has been carried out for 0.5-30 h, preferably 5-20 h, and most preferably 10 h, a 4-α-glucanotransferase is added to the reaction system.

Starch is a mixture of amylose and amylopectin of different chain lengths. In amylose, the glucose units are connected by α-1,4 glycosidic bonds, and amylopectin is connected to the starch backbone through α-1,6 glycosidic bonds. The α-glucan phosphorylase cannot hydrolyze the α-1,6 glycosidic bonds. When a debranching enzyme capable of hydrolyzing the α-1,6 glycosidic bonds in starch, i.e., isoamylase, is added to the reaction system, the yield of G1P and be increased. In addition, after the α-glucan phosphorylase hydrolyzes starch, starch derivatives or any mixture thereof to release G1P, the final product is maltose and maltotriose. In order to convert as many glucose units in starch to G1P as possible, a 4-α-glucanotransferase can be added to the reaction system, which can polymerize short-chain oligosaccharides to long-chain oligosaccharides, and the long-chain oligosaccharides can be reused by the α-glucan phosphorylase, thereby increasing the utilization rate of starch.

As a preferred embodiment, the enzymatic reaction of the present invention is carried out according to the following methods:

In a reaction system, isoamylase-treated soluble starch is taken as the substrate, and magnesium chloride, a phosphate, an ammonium salt, HEPES buffer (pH 7.0), α-glucan phosphorylase, phosphoglucomutase, phosphoglucose isomerase, glucosamine-6-phosphate deaminase, and an enzyme capable of catalyzing the dephosphorylation (preferably glucosamine-6-phosphate phosphatase) are added to go through a catalytic reaction to obtain glucosamine. Preferably, after the reaction has been carried out for a period of time, a 4-α-glucanotransferase is added to the reaction system.

In a further preferred embodiment, in a reaction system, 10 g/L isoamylase-treated soluble starch is taken as the substrate, 10 mM magnesium chloride, 20 mM potassium dihydrogen phosphate, 200 mM ammonium chloride, 100 mM HEPES buffer (pH 7.0), 2 U/mL α-glucan phosphorylase, 2 U/mL phosphoglucomutase, 3 U/mL phosphoglucose isomerase, 2 U/mL glucosamine-6-phosphate deaminase, and 2 U/mL an enzyme capable of catalyzing the dephosphorylation (preferably glucosamine-6-phosphate phosphatase) are added, and the reaction mixture goes through a catalytic reaction at 37° C. for 30 h to obtain glucosamine. Preferably, after the reaction has been carried out for 10 h, 1 U/mL 4-α-glucanotransferase is further added to the reaction system.

The present invention also provides the use of a glucosamine-6-phosphate deaminase and an enzyme capable of catalyzing the dephosphorylation (preferably glucosamine-6-phosphate phosphatase) in the preparation of glucosamine, preferably the use in catalyzing F6P to produce glucosamine.

The present invention also provides the use of an enzyme encoded by a nucleotide comprising a nucleotide sequence having at least 60%, at least 70%, at least 80%, at least 90%, at least 95%, at least 99% or 100% sequence identity with SEQ ID NO: 1 in the preparation of glucosamine, preferably the use in catalyzing glucosamine-6-phosphate (GlcN6P) to produce glucosamine (GlcN); preferably, the nucleotide is a nucleotide sequence having at least 60%, at least 70%, at least 80%, at least 90%, at least 95%, at least 99% or 100% sequence identity with SEQ ID NO: 1. Preferably, the enzyme comprises an amino acid sequence having at least 60%, at least 70%, at least 80%, at least 90%, at least 95%, at least 99% or 100% sequence identity with SEQ ID NO: 2; preferably, the enzyme has an amino acid sequence having at least 60%, at least 70%, at least 80%, at least 90%, at least 95%, at least 99% or 100% sequence identity with SEQ ID NO: 2. Preferably, the enzyme is a sugar phosphatase derived from *Thermococcus kodakarensis* (UniProt No. Q5JJ45).

The present invention also provides the glucosamine prepared by the above method.

The present invention uses an in vitro enzymatic reaction to prepare glucosamine for the first time, and especially uses a glucosamine-6-phosphate deaminase and an enzyme capable of catalyzing the dephosphorylation for catalyzing F6P to produce glucosamine for the first time. The method of the present invention can not only obtain the target product with a better conversion rate, but also has the advantages that the obtained product is safe to human body and the like. In addition, the method of the present invention can make use of a variety of raw materials, for example, a disaccharide or polysaccharide containing D-glucose units or any mixture thereof. Therefore, the method of the present invention has the advantages of cheap raw materials, rich raw material sources, low production cost, environmental friendliness, safety to human body and the like, and thus is suitable for popularization. In addition, the inventors also found that when starch, starch derivatives or any mixture thereof was used as the substrate for the production of glucosamine, the addition of isoamylase and 4-α-glucanotransferase could greatly increase the yield of the target product.

DETAILED DESCRIPTION OF THE INVENTION

The technical solutions of the present invention will be further described in detail with reference to the following specific examples. It should be understood that the following examples are only intended to examplarily illustrate and explain the present invention and should not be construed as limiting the scope of the present invention. All the technical solutions realized based on the above-mentioned contents of the present invention are covered in the protection scope of the present invention.

Unless otherwise specified, the raw materials and reagents used in the following examples are all commercially available products, or can be prepared by known methods.

The information of some materials used in the examples of the present invention is as follows:
Soluble starch, manufactured by ACROS Co., product No.: 424490020;
pET20b vector, Novagen, Madison, WI;
Escherichia coli BL21 (DE3), Invitrogen, Carlsbad, CA.

Figure 1:
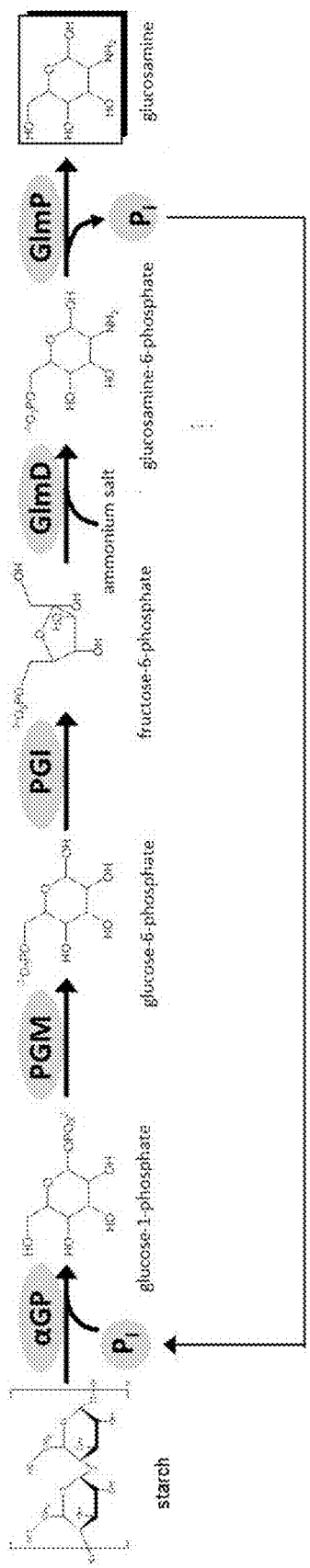
FIG. 1 is a schematic diagram of the in vitro enzymatic pathway for the preparation of glucosamine with starch as the substrate, wherein αGP represents α-glucan phosphorylase, PGM represents phosphoglucomutase, PGI represents phosphoglucose isomerase, GlmD represents glucosamine-6-phosphate deaminase, and GlmP represents glucosamine-6-phosphate phosphatase.
Figure 2:
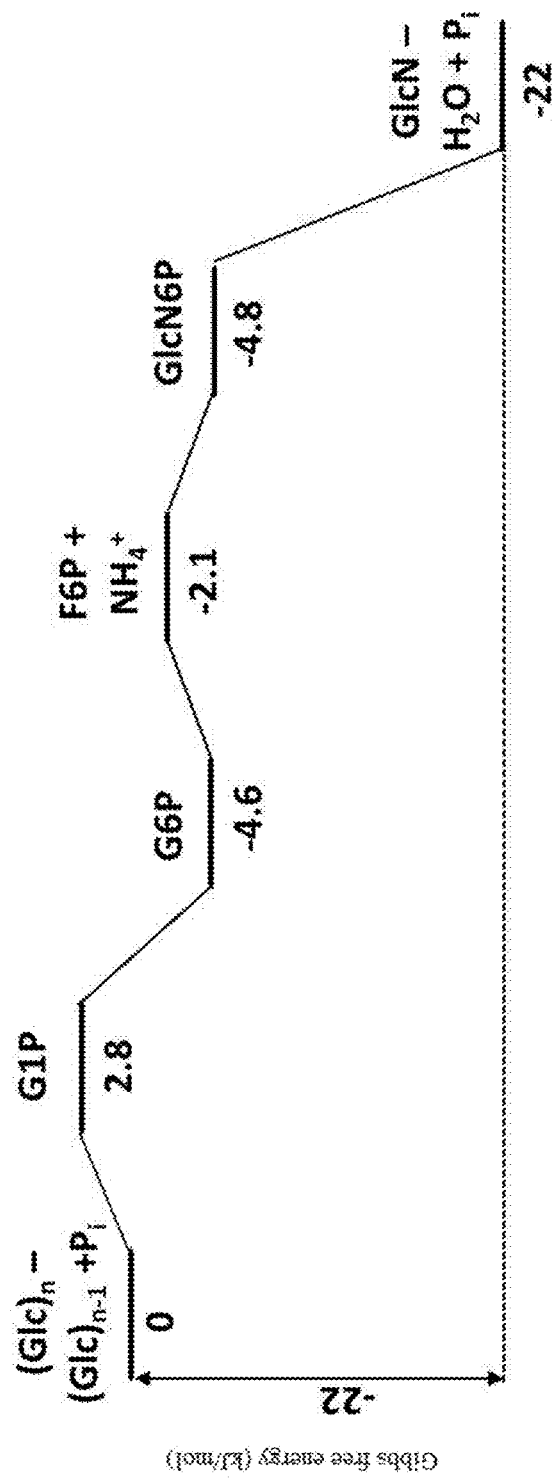
FIG. 2 shows the Gibbs energy change among the intermediates in the in vitro enzymatic pathway for the preparation of glucosamine with starch as the substrate.
Figure 3:
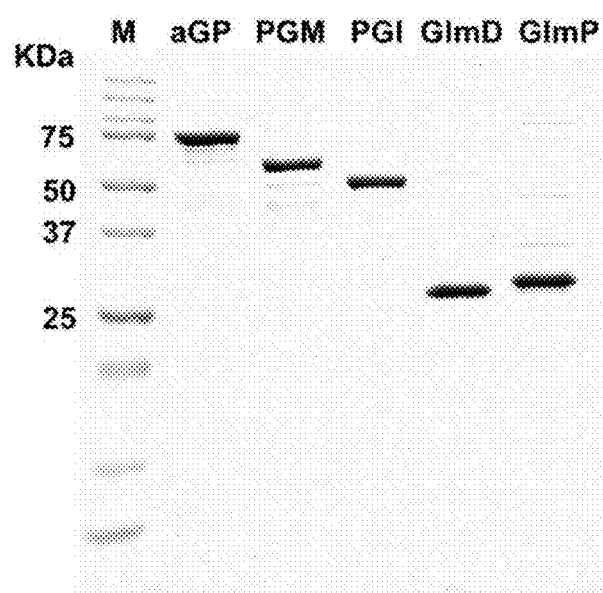
FIG. 3 shows the SDS-PAGE detection of the key enzymes for preparing glucosamine with starch as the substrate. M: Marker.

Example 1 Determination of Enzyme Activity in the Enzymatic Preparation of Glucosamine The catalytic pathway of converting starch to glucosamine in an in vitro enzymatic system is shown in FIG. 1, wherein the enzyme capable of catalyzing the dephosphorylation takes glucosamine-6-phosphate phosphatase as an example. FIG. 2 shows the Gibbs energy change among the intermediates in the enzymatic pathway of converting starch to glucosamine. In this example, (1) α-glucan phosphorylase is derived from Escherichia coli (Uniprot No. A0A0A0HB49); (2) phosphoglucomutase is derived from Clostridium thermocellum (Uniprot No. A3DEW8); (3) phosphoglucose isomerase is derived from Clostridium thermocellum (Uniprot No. A3DBX9); (4) glucosamine-6-phosphate deaminase is derived from Bacillus subtilis (Uniprot No. O35000); (5) the enzyme capable of catalyzing the dephosphorylation is glucosamine-6-phosphate phosphatase derived from Bacteroides thetaiotaomicron (Uniprot No. Q8A759). The genomic DNAs are available from the official website of ATCC (www.atcc.org). Through the method of Simple Cloning (You C, Zhang X Z, Zhang Y-H P. 2012. Simple cloning via direct transformation of PCR product (DNA Multimer) to Escherichia coli and Bacillus subtilis. Appl. Environ. Microbiol. 78(5):1593-5.), the above-mentioned genes were cloned into pET20b vector (Novagen, Madison, WI), to obtain the corresponding expression vectors pET20b-EcαGP, pET20b-CtPGM, pET20b-CtPGI, pET20b-BsGlmD, and pET20b-BtGlmP, respectively. The recombinant protein was expressed in Escherichia coli BL21 (DE3), and purified. The result of the protein purification is shown in FIG. 3.

The enzyme activity of the phosphoglucomutase derived from Clostridium thermocellum was measured in 100 mM HEPES buffer (pH 7.0) containing 10 mM magnesium chloride. With 10 mM glucose-1-phosphate as the substrate, the reaction was carried out at 37° C. for 10 min, and the amount of glucose-6-phosphate (G6P) produced was determined. The method for detecting the amount of G6P was as follows: 40 µl of sample solution containing G6P was taken, 200 µl of 100 mM HEPES buffer (pH 7.0) containing 2 mM magnesium chloride, 0.15 mM NAD$^+$ and 0.5 U/mL glucose 6-phosphate dehydrogenase (G6PDH) was added, the reaction was carried out at 37° C. for 30 min, the absorbance at 340 nm was measured, and the amount of the NADH produced was calculated. The experimental result showed that the specific activity of the phosphoglucomutase derived from Clostridium thermocellum at 37° C. was 20 U/mg.

The enzyme activity of the α-glucan phosphorylase derived from E. coli was measured in 100 mM HEPES buffer (pH 7.0) containing 10 mM magnesium chloride and 1 U/mL phosphoglucomutase. 5 g/L soluble starch was taken as the substrate, the reaction was carried out at 37° C. for 10 min, and the amount of the glucose-6-phosphate produced was determined. The experimental result showed that the specific activity of the α-glucan phosphorylase derived from E. coli at 37° C. was 5.6 U/mg.

The enzyme activity of the phosphoglucose isomerase derived from Clostridium thermocellum was measured in 100 mM HEPES buffer (pH 7.0) containing 10 mM magnesium chloride. 10 mM fructose-6-phosphate was taken as the substrate, the reaction was carried out at 37° C. for 10 min, and the amount of the glucose-6-phosphate produced was determined. The experimental result showed that the specific activity of the phosphoglucose isomerase derived from Clostridium thermocellum at 37° C. was 396 U/mg.

The enzyme activity of the glucosamine-6-phosphate deaminase derived from B. subtilis was measured in 100 mM HEPES buffer (pH 7.0) containing 10 mM magnesium chloride. 10 mM fructose-6-phosphate and 100 mM ammonium chloride were taken as the substrate, the reaction was carried out at 37° C. for 10 min, and the amount of the glucosamine-6-phosphate (GlcN6P) produced was determined. The method for detecting the amount of GlcN6P was as follows: 50 µl of sample solution containing GlcN6P was taken, 100 µl of acetylacetone reagent (which was prepared by dissolving 1.5 mL of acetylacetone in 50 mL of 1.25 mol/L sodium carbonate solution) was added; the resulting solution was boiled for 20 min, then cooled to room temperature, 1 mL of 96% (v/v) ethanol was slowly added, and then 100 µl of p-dimethylaminobenzaldehyde (DMAB) reagent (which was prepared by dissolving 1.6 g of DMAB in 30 mL of concentrated hydrochloric acid and 30 mL of 96% ethanol); the resulting solution was mixed uniformly, and allowed to stand at room temperature for 30 min; the absorbance at 530 nm was measured, and the amount of GlcN6P was calculated according to the standard curve. The experimental result showed that the specific activity of the glucosamine-6-phosphate deaminase derived from *B. subtilis* at 37° C. was 10 U/mg.

In this reaction pathway, an enzyme capable of catalyzing the dephosphorylation with specific dephosphorization activity for GlcN6P is one of the key points of the present invention. In 100 mM HEPES buffer (pH 7.0) containing 10 mM magnesium chloride, the dephosphorization activity of the above-mentioned enzyme capable of catalyzing the dephosphorylation on G1P, G6P, F6P and GlcN6P was measured. The experimental results were shown in Table 1. The glucosamine-6-phosphate phosphatase derived from *Bacteroides thetaiotaomicron* had higher specific activity for GlcN6P, and exhibited specific dephosphorization activity for GlcN6P. The sugar phosphatase (HAD superfamily) derived from *Thermococcus kodakarensis* had a dephosphorization activity of 0.011 U/mg for GlcN6P substrate at 70° C.

TABLE 1

Dephosphorization activity of two enzymes capable of catalyzing the dephosphorylation for different substrates

| | Specific activity (U/mg) | |
|---|---|---|
| Substrate | *Bacteroides thetaiotaomicron* Glmp [a] | Sugar phosphatase derived from *Thermococcus kodakarensis* [b] |
| G1P | 0 | 0 |
| G6P | 0.3 | 0 |
| F6P | 0.03 | 0.006 |
| GlcN6P | 3 | 0.011 |

[a]: specific activity measured at 37° C.;
[b]: specific activity measured at 70° C..

Example 2 In Vitro Enzymatic Preparation of Glucosamine from Soluble Starch

This example prepared glucosamine from soluble starch by in vitro enzymatic biosystem. First, five enzymes were recombinantly expressed: αGP from *Escherichia coli*, PGM from *Clostridium thermocellum*, PGI from *Clostridium thermocellum*, GlmD from *Bacillus subtilis*, and GlmP from *Bacteroides thetaiotaomicron* (Table 2).

TABLE 2

Information of enzymes used for the in vitro enzymatic preparation of glucosamine

| Enzyme | Enzyme No. | Source | Specific activity at 37° C. (U/mg) |
|---|---|---|---|
| α-glucan phosphorylase (αGP) | 2.4.1.1 | *E. coli* | 5.6 |
| phosphoglucomutase (PGM) | 5.4.2.2 | *C. thermocellum* | 20 |
| phosphoglucose isomerase (PGI) | 5.3.1.9 | *C. thermocellum* | 396 |
| glucosamine-6-phosphate deaminase (GlmD) | 3.5.99.6 | *B. subtilis* | 10 |
| glucosamine-6-phosphate phosphatase (GlmP) | — | *B. thetaiotaomicron* | 3 |

Figure 4:
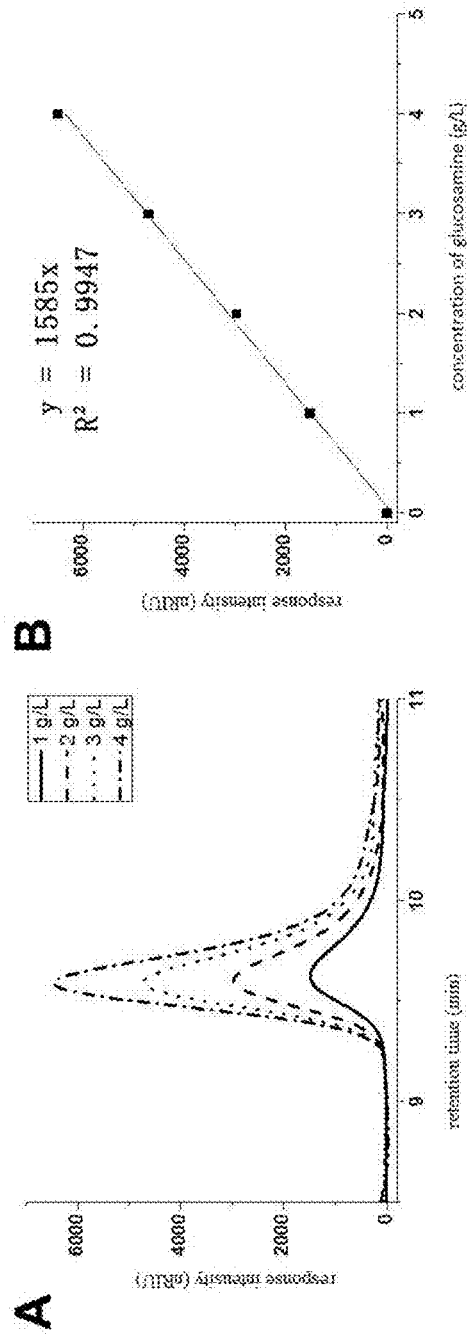
FIG. 4 shows the HPLC analysis results of glucosamine. 4A shows the HPLC peak graph of the glucosamine standard; and 4B shows the concentration of glucosamine as quantitatively analyzed by HPLC, wherein the concentration of the obtained glucosamine was quantified according to the intensity of the glucosamine peak.

Glucosamine was quantitatively analyzed by high performance liquid chromatography (HPLC). The chromatographic column used was an amino column, the mobile phase was 80% acetonitrile aqueous solution, the flow rate was 1 mL/min, the column temperature was 40° C., and the detector used was a differential refractive index detector. The detection of the standard sample was shown in FIG. 4A, and the retention time of glucosamine was about 9.6 min. The concentration of glucosamine was directly proportional to the response intensity of the HPLC characteristic peak of glucosamine, and the standard curve was shown in FIG. 4B.

Figure 5:
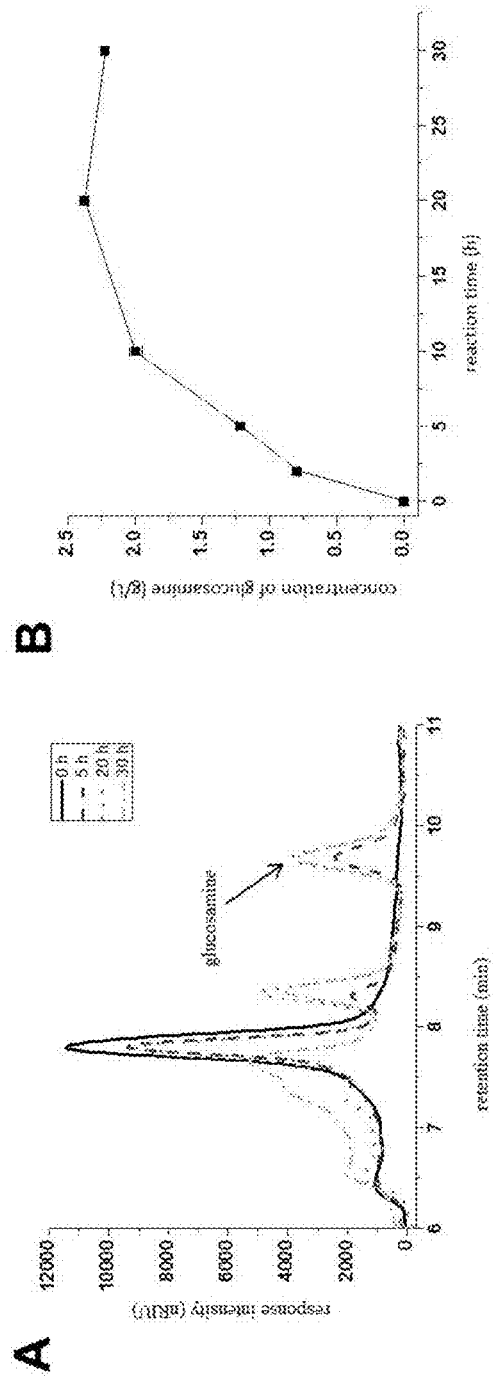
FIG. 5 shows the HPLC analysis of the in vitro enzymatic preparation of glucosamine from soluble starch in which glucosamine-6-phosphate deaminase is involved. 5A shows the HPLC analysis results of the in vitro enzymatic preparation of glucosamine from soluble starch; and 5B shows the reaction process curve of the in vitro enzymatic preparation of glucosamine from soluble starch.

0.5 mL of a reaction mixture containing 10 g/L soluble starch, 10 mM magnesium chloride, 20 mM potassium dihydrogen phosphate, 200 mM ammonium chloride, 100 mM HEPES buffer (pH 7.0), 1 U/mL αGP, 1 U/mL PGM, 1 U/mL PGI, 1 U/mL GlmD, 1 U/mL GlmP was reacted at 37° C. for 30 h. After completion of the reaction, an equal volume of acetonitrile was added to the reaction system to terminate the reaction, followed by centrifugation at 12,000 rpm for 10 min, and then the supernatant was taken to determine the concentration of glucosamine in the reaction solution by HPLC (FIG. 5A). When the reaction was carried out for 20 h, the concentration of glucosamine was 2.4 g/L, and the conversion rate was 24% (FIG. 5B).

The conversion rate of the product is calculated by the following formula:

$$\text{conversion rate (\%)} = \frac{\text{concentration of glucosamine produced (g/L)}}{\text{concentration of soluble starch initially added (g/L)}} \times 100\%$$

Example 3 In Vitro Enzymatic Preparation of Glucosamine from IA-Treated Soluble Starch Starch is polysaccharide having α-1,4 and α-1,6 mixed bonding, and thus cannot be completely hydrolyzed by α-glucan phosphorylase. Isoamylase (IA, EC 3.2.1.68) can hydrolyze the α-1,6 glycosidic bond in starch, and thus contributes the phosphorylation of the substrate by the α-glucan phosphorylase and increases the yield of glucosamine.

In this example, the isoamylase was derived from *Sulfolobus tokodaii* (UniProt No. Q973H3). The expression vector pET20b-StIA reported in the literature (Cheng, K. et al. Doubling Power Output of Starch Biobattery Treated by the Most Thermostable Isoamylase from an Archaeon *Sulfolobus tokodaii*. Sci. Rep. 5: 13184) was introduced into *E. coli* BL21 (DE3), to perform protein expression and purification.

To a 5 mM sodium acetate buffer (pH 5.5) containing 100 g/L soluble starch, 0.5 mM magnesium chloride and 1 U/mL isoamylase were added, and the mixture was allowed to react at 85° C. for 12 h.

Figure 6:
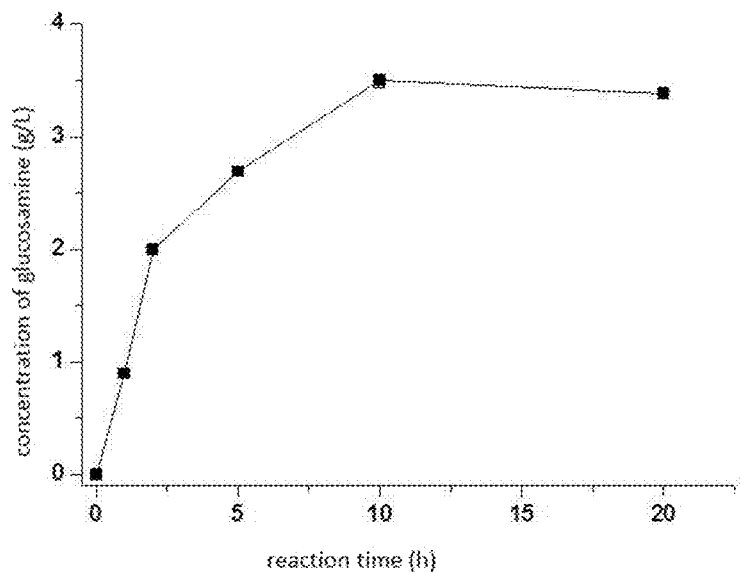
FIG. 6 shows the reaction process curve of the in vitro enzymatic preparation of glucosamine from IA-treated soluble starch.

0.5 mL of a reaction mixture containing 10 g/L isoamylase-treated soluble starch, 10 mM magnesium chloride, 20 mM potassium dihydrogen phosphate, 200 mM ammonium chloride, 100 mM HEPES buffer (pH 7.0), 1 U/mL αGP, 1 U/mL PGM, 1 U/mL PGI, 1 U/mL GlmD, and 1 U/mL GlmP was incubated at 37° C. for 20 h. Samples were taken at different times. An equal volume of acetonitrile was added to terminate the reaction, followed by centrifugation at 12,000 rpm for 10 min, and then the supernatant was taken to determine the concentration of glucosamine by HPLC. When the reaction was carried out for 10 h, the concentration of glucosamine was 3.5 g/L, and the conversion rate was 35% (FIG. 6).

Figure 7:
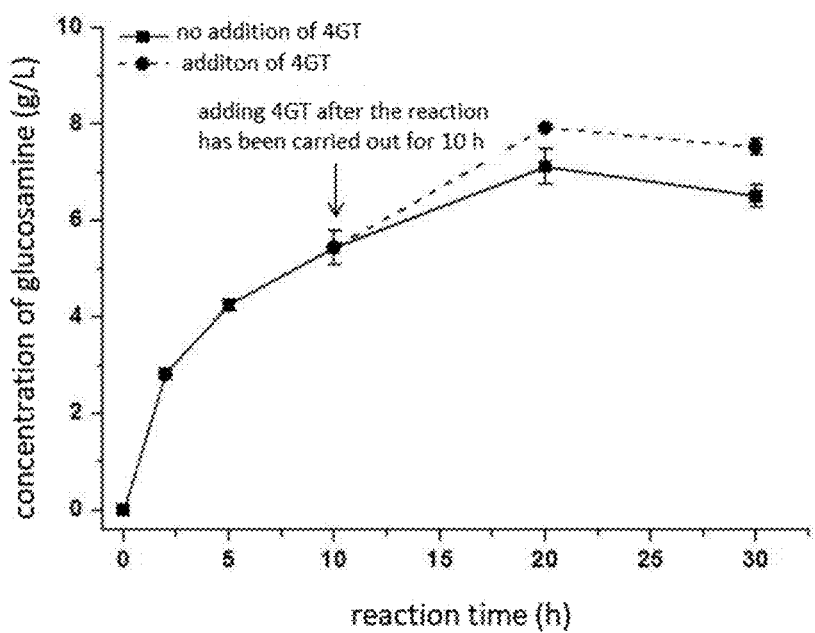
FIG. 7 shows the reaction process curve of the in vitro enzymatic preparation of glucosamine from IA-treated soluble starch after optimizing the enzyme concentration.

Example 4 In Vitro Enzymatic Preparation of Glucosamine from IA-Treated Soluble Starch after the Enzyme Concentration was Optimized 0.5 mL of a reaction mixture containing 10 g/L isoamylase-treated soluble starch, 10 mM magnesium chloride, 20 mM potassium dihydrogen phosphate, 200 mM ammonium chloride, 100 mM HEPES buffer (pH 7.0), 2 U/mL αGP, 2 U/mL PGM, 3 U/mL PGI, 2 U/mL GlmD, and 2 U/mL GlmP was incubated at 37° C. for 30 h. Samples were taken at different times. An equal volume of acetonitrile was added to terminate the reaction, followed by centrifugation at 12,000 rpm for 10 min, and then the supernatant was taken to determine the concentration of glucosamine by HPLC. When the reaction was carried out for 20 h, the concentration of glucosamine was 7.12 g/L, and the conversion rate was 71.2% (FIG. 7, solid line).

Example 5 Increasing the Yield of Glucosamine Through the Addition of 4-α-Glucanotransferase The isoamylase-treated soluble starch was phosphorylated by α-glucan phosphorylase, and the final remaining substrate was maltotriose and maltose. 4-α-Glucanotransferase (4GT, EC 2.4.1.25) can extend the sugar chain of short-chain malto-oligosaccharide, which can be further utilized by α-glucan phosphorylase and then converted to glucosamine, thereby increasing the yield of the product.

In this example, the 4-α-glucanotransferase was derived from *Thermococcus litoralis*, UniProt No. O32462. By using primers F2: TGTTTAACTTTAAGAAGGAGATATA ATGGAAAGAATAAACTTCATATTTG, R2: CAGTGGTGGTGGTGGTGGTGC TCGAGTCAAAGCTCCCTGAACCTTACCGTG, the gene of the 4-α-glucanotransferase was cloned into the pET20b vector through Simple Cloning method, to obtain the corresponding expression vector pET20b-St4GT. The expression vector was then introduced into *E. coli* BL21 (DE3), to perform protein expression and purification.

0.5 mL of a reaction mixture containing 10 g/L isoamylase-treated soluble starch, 10 mM magnesium chloride, 20 mM potassium dihydrogen phosphate, 200 mM ammonium chloride, 100 mM HEPES buffer (pH 7.0), 2 U/mL αGP, 2 U/mL PGM, 3 U/mL PGI, 2 U/mL GlmD, and 2 U/mL GlmP was incubated at 37° C. for 10 h. Then, 4GT was added to a final concentration of 1 U/mL, and the reaction was continued at 37° C. for 30 h. Samples were taken at different times. An equal volume of acetonitrile was added to terminate the reaction, followed by centrifugation at 12,000 rpm for 10 min, and then the supernatant was taken to determine the concentration of glucosamine in the reaction solution by HPLC. When the reaction was carried out for 20 h, the concentration of glucosamine was 7.93 g/L, and the conversion rate was 79.3% (FIG. 7, dashed line).

Figure 8:
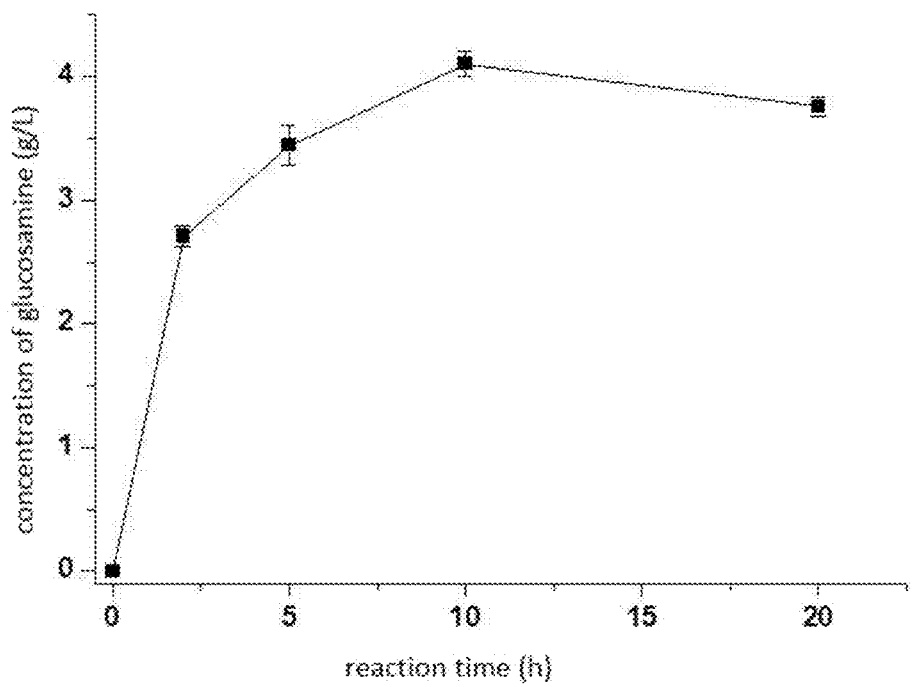
FIG. 8 shows the reaction process curve of the in vitro enzymatic conversion of sucrose to glucosamine.

Example 6 In Vitro Enzymatic Conversion of Sucrose to Glucosamine 0.5 mL of a reaction mixture containing 10 g/L sucrose, 10 mM magnesium chloride, 20 mM potassium dihydrogen phosphate, 200 mM ammonium chloride, 100 mM HEPES buffer (pH 7.0), 2 U/mL SP, 2 U/mL PGM, 3 U/mL PGI, 2 U/mL GlmD, and 2 U/mL GlmP was incubated at 37° C. for 20 h. Samples were taken at different times. An equal volume of acetonitrile was added to terminate the reaction, followed by centrifugation at 12,000 rpm for 10 min, and then the supernatant was taken to determine the concentration of glucosamine in the reaction solution by HPLC. When the reaction was carried out for 10 h, the concentration of glucosamine was 4.1 g/L, and the conversion rate was 41% (FIG. 8).

Figure 9:
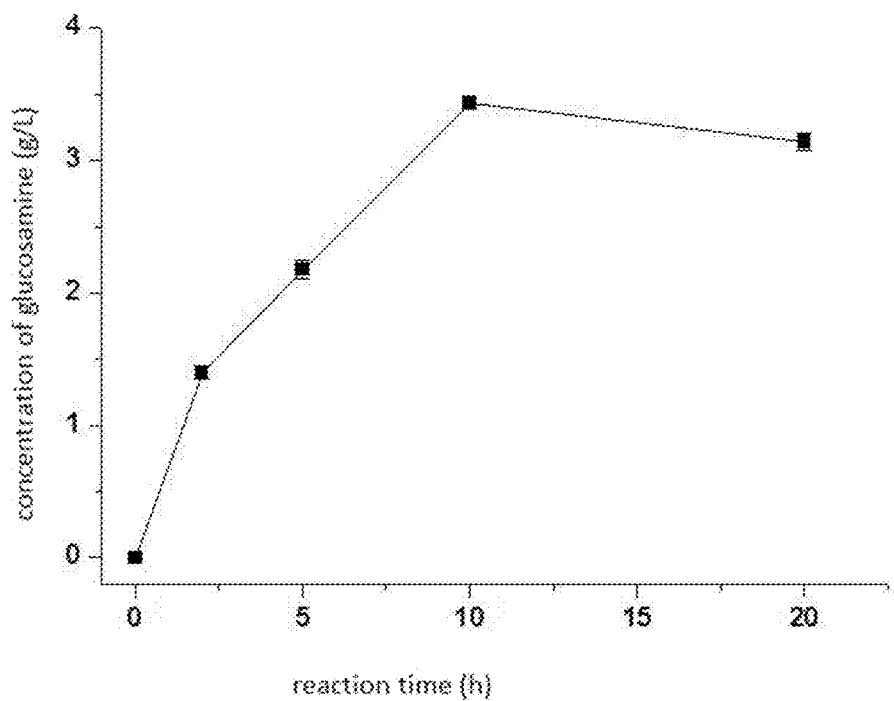
FIG. 9 shows the reaction process curve of the in vitro enzymatic conversion of cellodextrin to glucosamine.

Example 7 In Vitro Enzymatic Conversion of Cellodextrin to Glucosamine 0.5 mL of a reaction mixture containing 10 g/L cellodextrin (average degree of polymerization: 4.4), 10 mM magnesium chloride, 20 mM potassium dihydrogen phosphate, 200 mM ammonium chloride, 100 mM HEPES buffer (pH 7.0), 1 U/mL CDP, 1 U/mL CBP, 2 U/mL PGM, 3 U/mL PGI, 3 U/mL GlmD, and 2 U/mL GlmP was incubated at 37° C. for 20 h. Samples were taken at different times. An equal volume of acetonitrile was added to terminate the reaction, followed by centrifugation at 12,000 rpm for 10 min, and then the supernatant was taken to determine the concentration of glucosamine in the reaction solution by HPLC. When the reaction was carried out for 10 h, the concentration of glucosamine was 3.44 g/L, and the conversion rate was 34.4% (FIG. 9).

Example 8 In Vitro Enzymatic Conversion of Fructose-6-Phosphate to Glucosamine 0.5 mL of a reaction mixture containing 50 mM fructose-6-phosphate, 10 mM magnesium chloride, 200 mM ammonium chloride, 100 mM HEPES buffer (pH 7.0), 1 U/mL GlmD, and 1 U/mL GlmP was incubated at 37° C. for 10 h. Samples were taken at different times. An equal volume of acetonitrile was added to terminate the reaction, followed by centrifugation at 12,000 rpm for 10 min, and then the supernatant was taken to determine the concentration of glucosamine in the reaction solution by HPLC. When the reaction was carried out for 4 h, the concentration of glucosamine was 43.9 mM, and the conversion rate was 87.8%.

The embodiments of the present invention have been described above. However, the present invention is not limited to the above embodiments. Any modification, equivalent replacement, improvement and the like made without departing from the spirit and principle of the present invention shall fall within the protection scope of the present invention.

The invention claimed is:

1. A method for one-pot synthesis of glucosamine in vitro, comprising:
   forming a reaction mixture comprising fructose-6-phosphate (F6P), an ammonium salt, a glucosamine-6-phosphate deaminase (EC 3.5.99.6, GlmD), and a first enzyme in a reaction vessel;
   converting F6P and the ammonium salt to glucosamine-6-phosphate (GlcN6P) in the presence of the glucosamine-6-phosphate deaminase in the reaction vessel; and
   dephosphorylating GlcN6P in the presence of the first enzyme to produce glucosamine (GlcN) in the reaction vessel.

2. The method according to claim 1, wherein the ammonium salt is selected from the group consisting of ammonium sulfate, ammonium chloride, ammonium bisulfate, ammonium nitrate, ammonium carbonate, and ammonium bicarbonate, and mixtures thereof.

3. The method according to claim 1, wherein the reaction mixture further comprises the phosphoglucose isomerase, and the method further comprises converting glucose-6-phosphate (G6P) to F6P in the presence of the phosphoglucose isomerase (EC 5.3.1.9, PGI) in the reaction vessel.

4. The method according to claim 3, wherein the reaction mixture further comprises a phosphoglucomutase (EC 5.4.2.2, PGM), and the method further comprises converting glucose-1-phosphate (G1P) to G6P in the presence of the phosphoglucomutase (EC 5.4.2.2, PGM) in the reaction vessel.

5. The method according to claim 4, wherein the reaction mixture further comprises a second enzyme, and the method further comprises converting a substrate and a phosphate to G1P in the presence of the second enzyme in the reaction vessel, wherein the substrate is a disaccharide, polysaccharide, or a mixture of the disaccharide and polysaccharide, and the phosphate is selected from the group consisting of potassium dihydrogen phosphate, dipotassium hydrogen phosphate, sodium dihydrogen phosphate, and disodium hydrogen phosphate, and mixtures thereof.

6. The method according to claim 5, wherein the disaccharide is sucrose, and the second enzyme comprises sucrose phosphorylase (EC 2.4.1.7, SP), and/or
   the polysaccharide is selected from starch, starch derivatives, and mixtures thereof, and the second enzyme comprises α-glucan phosphorylase (EC 2.4.1.1, αGP).

7. The method according to claim 6, wherein the sucrose phosphorylase is Uniprot No. A0ZZH6 derived from *Bifidobacterium adolescentis*, or UniProt No. D9TT09 derived from *Thermoanaerobacterium thermosaccharolyticum*.

8. The method according to claim 6, wherein the α-glucan phosphorylase is Uniprot No. A0A0A0HB49 derived from *Escherichia coli*, Uniprot No. G4FEH8 derived from *Thermotoga maritima*, or Uniprot No. A3DCB6 derived from *Clostridium thermocellum*.

9. The method according to claim 6, wherein, when the substrate is starch, starch derivatives, or a mixture thereof, the second enzyme further comprises a 4-α-glucanotransferase (EC 2.4.1.25, 4GT).

10. The method according to claim 9, wherein the 4-α-glucanotransferases is UniProt No. O32462 derived from *Thermococcus litoralis*, UniProt No. L8AG91 derived from *Bacillus subtilis*, or UniProt No. Q59266 derived from *Clostridium butyricum*.

11. The method according to claim 5, wherein the polysaccharide comprises cellulose, cellulose derivatives, or mixtures thereof.

12. The method according to claim 11, wherein the reaction mixture further comprises cellobiose phosphorylase (EC 2.4.1.20, CBP), the polysaccharide further comprises cellobiose, and the cellobiose phosphorylase (EC 2.4.1.20, CBP) catalyzes a conversion of cellobiose and the phosphate to G1P.

13. The method according to claim 11, wherein the polysaccharide comprises cellulose, cellodextrin, or both, and the second enzyme comprises cellodextrin phosphorylase (EC 2.4.1.49, CDP).

14. The method according to claim 13, wherein the cellodextrin phosphorylase is UniProt No. A3DJQ6 derived from *Clostridium thermocellum*, or UniProt No. P77846 derived from *Clostridium stercorarium*.

15. The method according to claim 13, wherein the reaction mixture further comprises cellobiose phosphorylase (EC 2.4.1.20, CBP), and the polysaccharide degrades to form cellobiose in the reaction mixture, and the cellobiose phosphorylase (EC 2.4.1.20, CBP) catalyzes a conversion of cellobiose and the phosphate to G1P.

16. The method according to claim 15, wherein the cellobiose phosphorylase is UniProt No. A3DC35 derived from *Clostridium thermocellum*, or UniProt No. B9K7M6 derived from *Thermotoga neapolitana*.

17. The method according to claim 3, wherein the phosphoglucose isomerase is Uniprot No. A3DBX9 derived from *Clostridium thermocellum*, or UniProt No. Q5SLL6 derived from *Thermus thermophilus*.

18. The method according to claim 4, wherein the phosphoglucomutase is Uniprot No. A3DEW8 derived from *Clostridium thermocellum*, or UniProt No. Q68BJ6 derived from *Thermococcus kodakarensis*.

19. The method according to claim 5, wherein the reaction mixture further comprises an isoamylase (EC 3.2.1.68, IA), and the method further comprises hydrolyzing the α-1,6-glycosidic bonds in the substrate in the presence of the isoamylase (EC 3.2.1.68, IA) in the reaction vessel.

20. The method according to claim 19, wherein the isoamylase is UniProt No. Q973H3 derived from *Sulfolobus tokodaii*, or UniProt No. O32611 derived from *Flavobacterium* sp.

21. The method according to claim 1, wherein the glucosamine-6-phosphate deaminase is UniProt No. P0A759 derived from *Escherichia coli*, UniProt No. O35000 derived from *Bacillus subtilis*, UniProt No. V6TL01 derived from *Giardia lamblia*, or UniProt No. Q5JDU3 derived from *Thermococcus kodakarensis*.

22. The method according to claim 1, wherein the first enzyme is a glucosamine-6-phosphate phosphatase (GlmP)

that is UniProt Nos. P77475, P27848 or P0AE22 derived from *Escherichia coli*, or UniProt No. Q8A759 derived from *Bacteroides thetaiotaomicron*; or wherein the first enzyme is a sugar phosphatase that is UniProt No. Q5JJ45 derived from *Thermococcus kodakarensis*, which is encoded by a nucleotide comprises a nucleotide sequence having at least 90% sequence identity with SEQ ID NO: 1 or an amino acid sequence having at least 90% sequence identity with SEQ ID NO: 2.

* * * * *